though the present invention

United States Patent [19]
Hayashi et al.

[11] 4,213,918
[45] Jul. 22, 1980

[54] PROCESS FOR PRODUCING CLEAR AQUEOUS SOLUTION OF OLEFIN SULFONIC ACID

[75] Inventors: Akira Hayashi, Sakura; Haruo Ohkouchi; Kyozo Kitano, both of Chiba; Toshiaki Ogoshi, Funabashi, all of Japan

[73] Assignee: The Lion Fat & Oil Co., Ltd., Tokyo, Japan

[21] Appl. No.: 20,336

[22] Filed: Mar. 14, 1979

[30] Foreign Application Priority Data

Mar. 20, 1978 [JP] Japan .................................. 53-30979

[51] Int. Cl.$^2$ .......................................... C07C 143/02
[52] U.S. Cl. ................................................ 260/513 T
[58] Field of Search ........................ 260/513 T, 504 A

[56] References Cited

U.S. PATENT DOCUMENTS

4,139,498   2/1979   Kawakami et al. ............... 260/513 T

*Primary Examiner*—Alan Siegel
*Attorney, Agent, or Firm*—Armstrong, Nikaido, Marmelstein & Kubovcik

[57] ABSTRACT

Disclosed is a process for producing a clear aqueous solution of the magnesium salt of an olefin sulfonic acid by (i) sulfonating an olefin with an gaseous sulfur trioxide, (ii) neutralizing the resulting sulfonated olefin with an inorganic alkali consisting of magnesium hydroxide and/or oxide and an organic amine selected from water-soluble alkanol amines in specified amounts and, then, (iii) heating the neutralized mixture at a pH of from 6.0 to 8.0. Thus, a clear aqueous solution of the magnesium salt of an olefin sulfonic acid having no bad odor and no color deterioration can be obtained.

7 Claims, No Drawings

PROCESS FOR PRODUCING CLEAR AQUEOUS SOLUTION OF OLEFIN SULFONIC ACID

BACKGROUND OF THE INVENTION

1. Field of the Invention

The present invention relates to a process for producing a clear aqueous solution of the magnesium salt of an olefin sulfonic acid. More specifically, it relates to a process for producing a clear or transparent aqueous solution containing a high concentration of the magnesium salt of an olefin sulfonic acid by rapidly neutralizing and hydrolyzing a sulfonated olefin.

2. Description of the Prior Art

The magnesium salt of an olefin sulfonic acid is preferably used as an active agent (surfactant) for a liquid detergent due to its excellent frothing property. The magnesium salt of an olefin sulfonic acid can be produced by neutralizing and hydrolyzing a sulfonated olefin in the presence of magnesium hydroxide and/or magnesium oxide. However, since the magnesium hydroxide and oxide are only slightly soluble in water, the reaction rates of the neutralization and the hydrolysis are slow and, therefore, there is a problem that acidic hydrolysis of the sulfonated products occurs in the reaction system. That is to say, in the hydrolysis process of the sulfonated olefin, sultone present in the sulfonated olefin is hydrolyzed, and the hydroxyalkane sulfonic acid and alkene sulfonic acid, which are derived from the hydrolysis of the sultone, are neutralized. However, since the dissolving rate of the alkali (i.e. magnesium hydroxide andor oxide) into water is very slow, the hydrolysis occurs in the acidic side. This is because the amount of the acids formed by the hydrolysis of the sultone (i.e. the hydrolysis rate) is larger than that of the acid which is neutralized by the alkali (i.e. the alkali dissolving rate).

Such acidic hydrilysis necessarily causes the problems that a bad odor and color deterioration are generated in the reaction product. For this reason, in order to prevent the above-mentioned acidic hydrolysis, it is considered that the sulfonated olefin be neutralized and hydrolyzed in an extremely low concentration, or the sulfonated olefin be neutralized and hydrolyzed by using a large excess of the alkali. However, in the former process only a low concentration of the olefin sulfonate is obtained. In the latter process, due to the presence of the excess alkali, the reaction product becomes opaque or unclear and, occasionally, even precipitates are formed in the reaction product. These opacity and precipitates caused by the presence of the excess alkali can be removed to a certain extent by removing the unreacted alkali by means of a filtration or by consuming the unreacted alkali with the addition of an appropriate inorganic or organic acid. However, a reaction product having a high viscosity is not easily filtered. In the case where the reaction product is diluted in order to make the filtration smooth, the concentration of the olefin sulfonate unpreferably decreased. On the other hand, there are problems in the method for removing the unreacted alkali with the addition of the additional acid after the reaction, in that not only does the operation become troublesome but, also, the extra salts are incorporated into the reaction products.

SUMMARY OF THE INVENTION

The objects of the present invention are to obviate the above-mentioned problems of the conventional process for producing the magnesium salt of an olefin sulfonic acid, and to provide a process which is capable of producing an aqueous clear solution of the magnesium salt of the olefin sulfonic acid containing a high concentration thereof.

More specifically, the object of the present invention is to produce an aqueous clear solution containing a high concentration of the magnesium salt of the olefin sulfonic acid, while causing no substantial generation of the acidic hydrolysis and neither specifically diluting the sulfonated olefin nor using a large excess of the alkali.

Other objects and advantages of the present invention will be apparent from the description set forth hereinbelow.

In accordance with the present invention, there is provided a process for producing a clear aqueous solution of the magnesium salt of an olefin sulfonic acid comprising the steps of:

(a) sulfonating at least one olefin having 8 to 22 carbon atoms by a gaseous sulfur trioxide diluted with an inert gas;

(b) neutralizing at least a portion of the sulfonic acid contained in the resulting sulfonated olefin by mixing said sulfonated olefin with (i) an aqueous inorganic alkali dispersion containing magenesium hydroxide, magenesium oxide or a mixture thereof and (ii), at least one organic alkali selected from water-soluble alkanol amines, in such amounts that the amount of the total alkalis is within the range of from 1.0 to 1.1 chemical equivalent based on 1.0 chemical equivalent of the sulfonated olefin and that the amount of the inorganic alkali is within the range of from 0.75 to 0.95 chemical equivalent based on 1.0 chemical equivalent of the sulfonated olefin, and;

(c) heating the resulting neutralization mixture at a pH of from 6.0 to 8.0 to thereby hydrolyze the mixture.

DESCRIPTION OF THE PREFERRED EMBODIMENTS

In the process according to the present invention, an olefin or olefins having 8 to 22 carbon atoms are sulfonated by a gaseous $SO_3$ diluted with an inert gas such as dry air, nitrogen and the like in any conventional procedure. Such sulfonation procedures are well known in the art (for example, please refer to U.S. Pat. Nos. 3,427,342 and 3,839,391). The olefins used in the sulfonation reaction preferably include 1-octene, 1-decene, 1-dodecene, 1-tetradecene, 1-hexadecene, 1-heptadecene, 1-octadecene, 1-eicosene, 1-docosene and the like, as well as internal olefins in which the double bond is present in the inner part of the molecular chain (i.e. not in the outermost part of end of the molecular chain), such as, for example, 2-dodecene, 3-dodecene, 4-dodecene, 5-dodecene, 6-dodecene, 2-tetradecene, 3-tetradecene, 4-tetradecene, 7-tetradecene, 2-hexadecene, 3-hexadecene, 5-hexadecene and 8-hexadecene.

In addition, vinylidene type olefins, such as, for example, 2-methyl-dodecene-1,2-ethyl-dodecene-1,2-ethyl-hexadocene-1and 2-hexyl-decene-1, can be used in the present invention. However, since vinylidene type olefins produce only a small amount of sultone during the sulfonation, the above-mentioned problems of the hydrolysis are small compared to the case of the α-olefins and internal olefins.

According to the neutralization step of the present invention, the sulfonated olefin is mixed with an aqueous inorganic alkali dispersion containing magneisum hydroxide and/or oxide and an organic alkali or alkalis consisting of water-soluble alkanol amines. The amount of the total alkalis mixed with the sulfonated olefin is within the range of from approximately 1.0 to approximately 1.1 chemical equivalent, based on 1.0 equivalent of the sulfonated olefin. When the amount of the total alkalis is less than 1.0 equivalent, since pH of the system becomes 6 or less, unpreferable color change is caused and also unpreferable odor is generated. On the other hand, when the amount of the total alkalis is more than 1.1 equivalent, since inorganic alkali substances are formed in the system the resultant liquid unpreferably becomes turbid. The amount of the inorganic alkali is within the range of from approximately 0.75 to approximately 0.95 chemical equivalent based on 1.0 chemical equivalent of the sulfonated olefin. Thus, the amount of the organic alkali is within the range of from approximately 0.05 to approximately 0.35 chemical equivalent based on 1.0 chemical equivalent of the sulfonated olefin. When the amount of the inorganic alkali is less than 0.75 equivalent, since the gelation occurs and the neutralization becomes incomplete, unpreferable color deterioration is cause. On the other hand, when the amount of the inorganic alkali is more than 0.95 equivalent, the resultant liquid unpreferably becomes turbid due to the formation of inorganic alkalis.

The water-soluble akanol amines employed in the present invention preferably include, such as, for example, monoethanolamine, diethanolamine, triethanolamine, N,N-dimethylethanolamine, N,N-diethylethanolamine, N-methylethanolamine, N-ethylethanolamine, aminoethylethanolamine, and the like.

The above-mentioned inorganic amine and organic amine can be simultaneously mixed with the sulfonated olefin. It is, however, preferable that the aqueous dispersion containing the inorganic alkali be first mixed with the sulfonated olefin, whereby at least a portion of the sulfonic acid contained in the sulfonated olefin is neutralized, and then, the organic alkali is mixed with the resulting mixture. This is because, if the organic alkali is first used, since the amount of the alkali is relatively small with respect to the amount of the sulfonic acid in the sulfonated products, unpreferable changes of the color and odor are stable to be caused due to the fact that the liquid becomes acidic prior to the hydrolysis. In this case, the incorporating of a salt of an organic acid into the aqueous inorganic alkali dispersion prior to the mixing of the inorganic acid with the sulfonated olefin is more preferable for the reasons that the period of time required for the neutralization is reduced and that the hydrolysis smoothly proceeds. The salts an organic acid include, for example, sodium benzoate, sodium citrate, sodium malate, sodium tartrate, sodium gluconate, sodium ethylenediamine tetraacetate (EDTA-Na), sodium nitrilotriacetate (NTA-Na) and the like. The neutralization reaction is preferably carried out at a temperature of not more than approximately 50° C., and more preferably between 40° and 50° C. The neutralization reaction is carried out for a period of time sufficient to neutralize at least a portion of, and preferably most of, a free sulfonic acid present in the sulfonated olefin to the magnesium salt.

The neutralized mixture thus obtained is then hydrolyzed by heating the mixture at a pH of from approximately 6.0 to approximately 8.0. In the case where the neutralization reaction is conducted in the absence of the organic alkali, the required amount of the organic amine must be added to the neutralized mixture prior to the hydrolysis. The hydrolysis is preferably effected at a temperature of from approximately 110° C. to approximately 180° C. When the pH is less than 6.0, unpreferable changes of the color and odor are caused, whereas when the pH is more than 8.0, the liquid unpreferably becomes turbid due to the formation of the inorganic alkalis (MgO and Mg(OH)$_2$). The reaction mixture to be hydrolyzed is generally alkaline, and there is a case where the pH of the reaction mixture is beyond 8.0, especially when a respectively large amount of the organic alkali is added to the reaction mixture just before the hydrolysis is started. However, once the reaction mixture begins to be heated, the pH of the reaction mixture can be maintained within the range of from 6.0 to 8.0, since the alkali present in the reaction mixture is consumed by the generation of the hydrolysis of the sultone contained in the reaction mixture. Thus, the precipitation of the inorganic alkali (magnesium oxide and/or hydroxide) can be prevented.

As mentioned, in detail, hereinabove, according to the present invention, since the hydrolysis of the sultone contained in the sulfonated olefin is conducted in the presence of the water-soluble alkanol amine, not only the hydrolysis reaction can be rapidly effected, but also, the generation of the aforementioned acidic hydrolysis can be depressed. In addition, the precipitation of the magnesium compound can be prevented. Therefore, according to the present invention, an aqueous clear solution of the magnesium salt of an olefin sulfonic acid or acids can be obtained without causing color deterioration (or color change) and without generating a bad odor. Furthermore, since the sulfonated olefin is neutralized and hydrolized in the present invention without being subjected to any special dilution, an aqueous solution containing a relatively high amount (e.g. approximately 20 through 50%) of the magnesium salt of the olefin sulfonic acid can be produced.

Although the reaction mechanism of the hydrolysis according to the present invention is not clearly understood, it is believed that the following reactions are repeated. That is, both the alkanol amine and the magnesium compound are simultaneously reacted with the hydrolysis products of the sultone present in the sulfonated olefin, whereby the alkanol amine salt and the magnesium salt, of the hydrolysis products are formed, and the former (i.e. the alkanol amine salt of the hydrolysis products) is then reacted with the unreacted magnesium compound to from the magnesium salt of the hydrolysis products and free alkanol amine.

The present invention now will be further illustrated by the following examples. However, it should be understood that these are presented merely to explain and not to limit the invention, and that numerous changes may be made without departing from the spirit and the scope of the invention as hereinafter claimed.

EXAMPLE $C_{16}$–$C_{18}$, $C_{14}$ and $C_{12}$–$C_{14}$ α-olefins were separately sulfonated with gaseous SO$_3$ diluted by dry air using a falling film type sulfonation reactor, as disclosed in U.S. Pat. No. 4,036,596, under the conditions of a mole ratio of SO$_3$/olefin of 1.14 and a temperature of 55°–60° C. 200 g of each sulfonated olefin (olefin sulfonates) thus obtained were added to an aqueous dispersion containing Mg(OH)$_2$ or MgO in the amount shown in Table 1. Thus, the sulfonated olefin was neutralized. Into the neutralized mixture alkanol amine listed in Table 1 was added in the amount shown in Table 1 and, then, the mixture was heated at a temperature of 140° to 160° C. for 20 min. Thus, the mixture was hydrolized to form an aqueous solution of the magnesium salt of the α-olefin sulfonic acid.

The amount of $Mg(OH)_2$ or MgO used, the amount of the alkanol amine used, the hydrolysis conditions and the properties of the resultant aqueous solution of the magnesium salt of α-olefin sulfonic acid are shown in Table 1. In Table 1, A represents the $C_{16}$–$C_{18}$ α-olefin sulfonates, B the $C_{14}$ α-olefin sulfonates and C the $C_{12}$–$C_{14}$ α-olefin sulfonates. The appearance (turbidity) and color of the aqueous solution was checked by the naked eye and rated as follows.

O ... good
Δ ... fair
X ... poor

Table I

| Run No. | 1*1 | 2*1 | 3 | 4*1 | 5*1 | 6 | 7 | 8 | 9 | 10 | 11 | 12 | 13 | 14 | 15*1 | 16 |
|---|---|---|---|---|---|---|---|---|---|---|---|---|---|---|---|---|
| Kind of Olefin Sulfonate | A | A | A | A | A | A | A | A | B | B | B | C | C | C | A | A |
| Alkali | | | | | | | | | | | | | | | | |
| Mg(OH)₂ | 22.7 | 20.6 | 19.6 | 19.6 | 16.5 | 16.5 | 18.5 | | 21.2 | 21.2 | 21.2 | 22.6 | 22.6 | | 12.4 | 9.8 |
| MgO | | | | | | | | 13.5 | | | | | | 14.9*2 | | 6.8 |
| Equivalent ratio based | 1.10 | 1.00 | 0.95 | 0.95 | 0.80 | 0.80 | 0.90 | 0.95 | 0.90 | 0.90 | 0.90 | 0.90 | 0.90 | 0.86 | 0.6 | (wt. %) |
| Monoethanol amine | | | | | | | | 4.2 | | | | 6.1 | | | 25.2 | 4.2 |
| Diethanol amine | | | | | | | | | | | | | 10.6 | | | |
| Triethanol amine | | | | | | | | | | | | | | 22.4 | | |
| N,N-dimethylethanol amine | | | | | | | | | 8.7 | | | | | | | |
| N,N-diethylethanol amine | | | | | | | | | | 11.7 | | | | | | |
| N-methylethanol amine | | | | | | | | | | | 7.5 | | | | | |
| Aminoethylethanol amine | | | 3.4 | 10.5 | 7.0 | 13.0 | 7.0 | | | | | | | | | |
| Equivalent ratio based on sulfonate | | | 0.60 | 0.20 | 0.13 | 0.25 | 0.13 | 0.07 | 0.10 | 0.10 | 0.10 | 0.10 | 0.10 | 0.15 | 0.42 | 0.07 |
| Equivalent ratio (total alkali/sulfonate) | 1.10 | 1.00 | 1.01 | 1.15 | 0.93 | 1.05 | 1.03 | 1.02 | 0.10 | 0.10 | 0.10 | 0.10 | 0.10 | 1.01 | 1.02 | 1.02 |
| Hydrolysis Temperature (°C.) | 160 | 160 | 160 | 160 | 160 | 160 | 160 | 160 | 150 | 150 | 150 | 140 | 140 | 140 | 160 | 160 |
| Hydrolysis pH | 6–8.5 | 2–4 | 6–7 | 8–9 | 2–4 | 7–8 | 6–8 | 6–8 | 6–7 | 6–7 | 6–7 | 6–7 | 6–7 | 6–8 | 6–8 | 6–8 |
| Property of Aqueous Solution of Magnesium Salt | | | | | | | | | | | | | | | | |
| Concentration (wt. %) | 35 | 35 | 35 | 35 | 35 | 35 | 35 | 35 | 40 | 40 | 40 | 45 | 45 | 45 | 35 | 35 |
| Appearance (turbidity) | X | | | X | | | | | | | | | | | | |
| Color | Δ | X | | | X | | | | | | | | | | X | |

*1 Comparative Example
*2 6 g of sodium citrate was also contained in the aqueous dispersion.

As is clearly indicated in Table 1 above, in Run Nos. 1 and 2, although the amounts of the total alkali were within the scope of the present invention, aqueous solutions having good properties could not be obtained because no alkanol amine was used. Similarly, in Run Nos. 4 and 5, although the alkanol amine was used together with the magnesium compound, aqueous solutions having good properties could not be obtained because the amounts of the total alkali were outside of the scope of the present invention. In Run No. 4, since the pH was too high during the hydrolysis, $Mg(OH)_2$ was preciptiated in the solution, so that the solution became turbid. In Run No. 5, the color of the aqueous solution of the magnesium salt was changed due to the fact that the pH was too low during the hydrolysis.

Contrary to the above mentioned runs, in Run Nos. 3 and 6 through 14 and 16, according to the present process, aqueous solutions of the maagnesium salt of the olefin sulfonic acids having good properties were invariably obtained.

What we claim is:

1. A process for producing a clear aqueous solution of the magnesium salt of an olefin sulfonic acid comprising the steps of:
    (a) sulfonating at least one olefin having 8 to 22 carbon atoms by a gaseous sulfur trioxide diluted with an inert gas;
    (b) neutralizing at least a portion of the sulfonic acid contained in the resulting sulfonated olefin by mixing said sulfonated olefin with (i) an aqueous inorganic alkali dispersion containing magnesium hydroxide, magnesium oxide or a mixture thereof and (ii) at least one water-soluble alkanol amine, in such amounts that the total amount of said inorganic alkali and said alkanol amine is within the range of from 1.0 to 1.1 chemical equivalent based on 1.0 chemical equivalent of the sulfonated olefin and that the amount of the inorganic alkali is within the range of from 0.75 to 0.95 chemical equivalent based on 1.0 chemical equivalent of the sulfonated olefin, and;
    (c) heating the resulting neutralization mixture at a pH of from 6.0 to 8.0 to thereby hydrolyze the mixture.

2. A process as claimed in claim 1, wherein said neutralization is effected by first mixing the aqueous inorganic alkali dispersion with the sulfonated olefin to thereby neutralize at least a portion of the sulfonic acid contained in the sulfonated olefin and, then, by mixing the water-soluble alkanol amine with the resulting neutralized mixture.

3. A process as claimed in claim 1, wherein said neutralization is effected at a temperature of not more than approximately 50° C.

4. A process as claimed in claim 1, wherein said hydrolysis is effected at a temperature within the range of from approximately 110° C. to approximately 180° C.

5. A process as claimed in claim 1, wherein said water-soluble alkanol amine are monoethanolamine, diethanolamine, triethanolamine, N,N-dimethylethanolamine, N,N-diethylethanolamine, N-methylethanolamine, N-ethylethanolamine and aminoethylethanolamine.

6. A process as claimed in claim 2, wherein said aqueous inorganic alkali dispersion further contains a salt of an organic acid.

7. A process as claimed in claim 6, wherein said salt is selected from the group consisting of sodium benzoate, sodium citrate, sodium malate, sodium tartrate, sodium gluconate, sodium ethylenediamine tetraacetate and sodium nitriloacetate.

* * * * *